United States Patent [19]

Houseman et al.

[11] Patent Number: 4,738,534

[45] Date of Patent: Apr. 19, 1988

[54] VERTICAL BEAM SPECTROPHOTOMETER

[75] Inventors: Kenneth R. Houseman, Racine, Wis.; David C. Wender, Vernon Hills, Ill.; Lawrence G. Banovez, Kenosha, Wis.; Mieczyslaw Wroblewski, Lake Forest, Ill.

[73] Assignee: Abbott Laboratories, North Chicago, Ill.

[21] Appl. No.: 30,931

[22] Filed: Mar. 26, 1987

[51] Int. Cl.$^4$ .................. G01N 21/03; G01N 21/31
[52] U.S. Cl. .................................. 356/414; 356/418; 356/442; 436/807; 436/527
[58] Field of Search .................. 356/414, 418, 442; 442/102; 436/527, 805

[56] References Cited

U.S. PATENT DOCUMENTS

| | | | |
|---|---|---|---|
| 3,992,631 | 11/1976 | Harte | 250/365 |
| 4,147,752 | 4/1979 | Suovaniemi et al. | 422/57 |
| 4,245,052 | 1/1981 | Lund | 422/102 X |
| 4,290,997 | 9/1981 | Suovaniemi | 422/73 |
| 4,448,534 | 5/1984 | Wertz et al. | 356/442 X |
| 4,510,119 | 4/1985 | Hevey | 422/102 X |
| 4,579,828 | 4/1986 | Ali | 422/102 X |

FOREIGN PATENT DOCUMENTS

85/01885  9/1985  PCT Int'l Appl. .............. 35/2

Primary Examiner—R. A. Rosenberger
Assistant Examiner—S. McGowan
Attorney, Agent, or Firm—Alan W. Kowalchyk

[57] ABSTRACT

A vertical beam spectrophotometer for measuring the light absorption of an assay prepared using standard wet chemistry procedures and conventional solid phase coated bead technology is disclosed. The spectrophotometer measures the absorption of the assay in a conventional reaction cuvette with the bead remaining in the cuvette. The light source of the spectrophotometer illuminates the bead, which diffuses the light into the surrounding assay solution. A lense projects the diffused light onto a photocell which converts it into an electrical signal having magnitude related to the light absorption of the assay. The signal is processed in a known manner by conventional processing circuitry to obtain an absorption value.

19 Claims, 1 Drawing Sheet

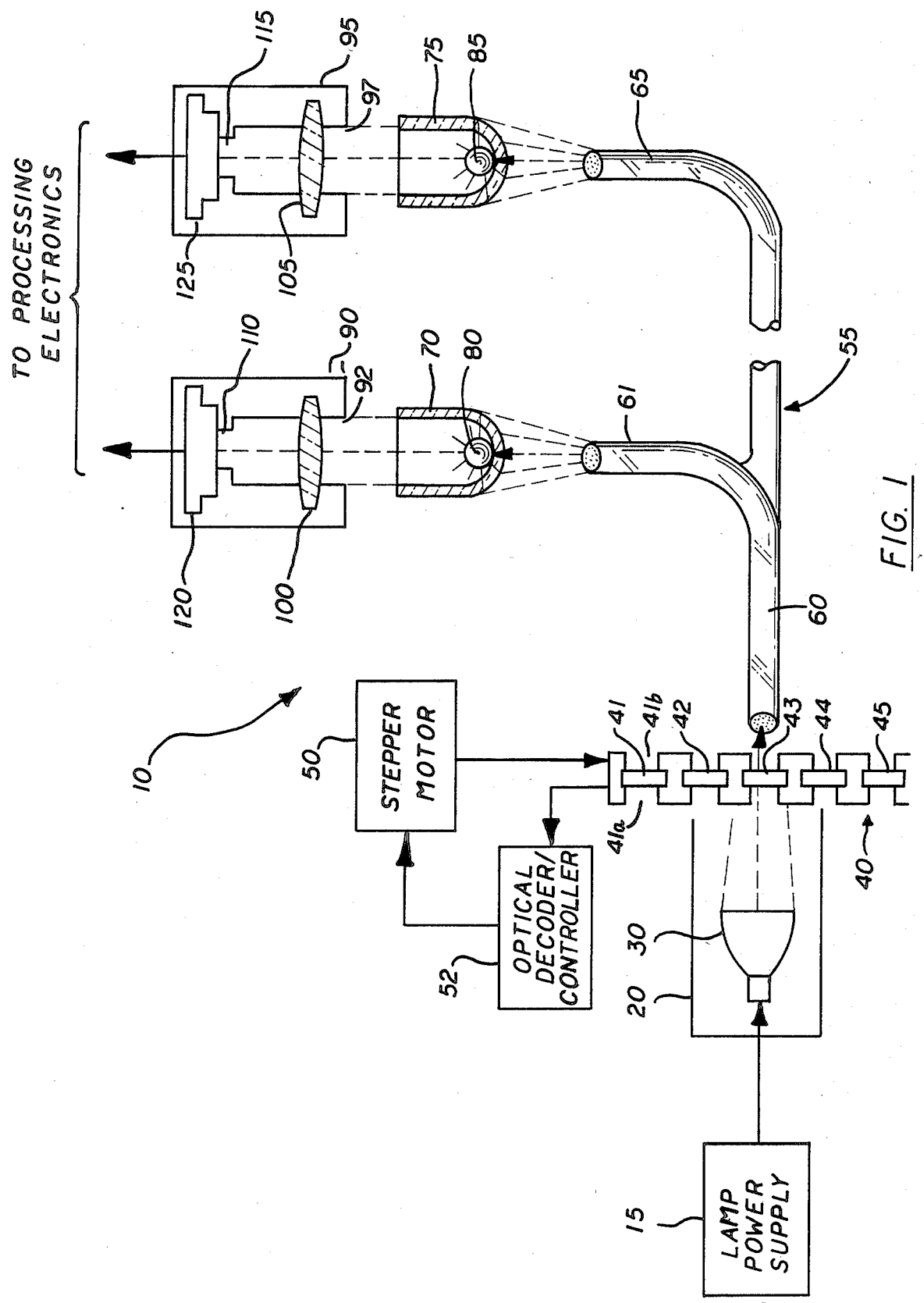

VERTICAL BEAM SPECTROPHOTOMETER

BACKGROUND OF THE INVENTION

1. Field of the Invention

This invention relates generally to apparatus and methods for measuring assays and more specifically to a spectrophotometric apparatus and method for measuring assays prepared using standard wet chemistry procedures and conventional solid phase technology wherein the solid phase remains in the reaction cuvette during the measurement and is utilized as the light source for the measurement.

2. Statement of the Related Art

The use of spectrophotometric apparatus and methods to measure assays prepared using standard wet chemistry procedures and conventional solid phase, coated bead technology is well known. One typical procedure for performing and measuring an enzyme immunoassay (EIA), for example, involves coating a spherical plastic bead (the carrier or substrate) with an antibody or antigen which is the compliment of the antibody or antigen being tested for. The bead is then put through a series of sample exposure, reagent exposure, incubation, and washing steps that cause the surface of the bead to become coated with one or more layers (solid phases) of the antigen or antibody being tested for and the complimentary antigen or antibody. The antigen or antibody forming the outer layer is labelled with an enzyme such as horseradish peroxidase, for example. The coated bead is then exposed to a solution containing a chromophore such as OPD which reacts with the enzyme and colors the solution. The optical density of the coloration, i.e. the degree of optical development of the solution, is indicative of the concentration of the antigen or antibody being tested for in the original sample. A conventional spectrophotometer measures the assay by illuminating the solution with one or more beams of light having one or more selected wavelengths in the visible light range corresponding to spectral components of the colored solution. A detector measures the absorbance of the selected wavelengths by the solution. The measured absorbance values are then processed in a known manner to obtain the concentration of the antigen or antibody of interest.

Automated assay machines that spectrophotometrically measure batches of assays prepared using coated bead technology, such as the EIA just described, are known. Typically in such machines, a plurality of such assays are formed in a corresponding plurality of reaction wells or cuvettes of a molded plastic tray. The coated beads are removed from the cuvettes by a mechanical apparatus and placed in separate glass or plastic tubes before chromophore is added and measurements taken.

In order to improve the processing speed and throughput of such equipment, it is advantageous to be able to measure the assays without removing the coated beads from the reaction cuvettes. Attempts have been made in the past to spectrophotometrically measure an assay while retaining the solid phase in the reaction cuvette during the measurement. However, these attempts have required the use of specially designed assay components to avoid contact between the solid phase and the light beam during the measurement.

Cetus PCT Pat. No. 86/02168, for example, discloses an automated assay machine which spectrophotometrically measures the absorption of visible light by a reacted assay with the bead in the reaction well. The Cetus system requires specially designed reaction trays having individual wells with slanted, slotted bottom surfaces or separate sub-wells in order to maintain the bead outside the path of the vertical light beam which passes through the solution during the measurement.

Suovaniemi et al. U.S. Pat. No. 4,147,752 discloses a substrate for a solid phase assay that allows the assay to be measured without removing the substrate. The substrate is a specially designed form piece that must be positioned in the cuvette with a specific orientation. In one embodiment, the form piece is shaped as a ring to facilitate spectrophotometric measurement of the assay without contact between the light beam and the form piece.

In view of the above described need and the limitations of the prior art, it is an object of the present invention to provide a spectrophotometric apparatus that is capable of measuring assays prepared using conventional wet chemistry procedures and solid phase technology with the solid phase remaining in the reaction well during the measurement, and that is particularly suitable for use in automated assay equipment.

It is another object of the invention to provide such an apparatus that utilizes the solid phase itself as a light diffusing source to accomplish the measurement.

It is still another object of the invention to provide such an apparatus that is used advantageously with conventional reaction trays and coated beads.

SUMMARY OF THE INVENTION

The foregoing objects and attendant advantages thereof are obtained by providing a spectrophotometer having a light source that illuminates a solid phase such as a conventional coated bead to cause the solid phase to diffuse light into a surrounding solution. The spectrophotometer includes an optical device which projects the light diffused by the solid phase onto an optoelectronic device which converts the light into an electrical signal having a parameter related to the absorption of the assay.

In another aspect of the invention, the light source illuminates a plurality of solid phases simultaneously. A corresponding plurality of optical devices simultaneously project the light diffused by each of the solid phases onto a corresponding plurality of optoelectronic devices which convert the light into a corresponding plurality of electrical signals each having a parameter related to the absorption of the corresponding assay.

BRIEF DESCRIPTION OF THE DRAWING

The novel features that are believed to be characteristic of the invention are set forth in the appended claims. The invention itself, together with the foregoing objects and attendant advantages thereof, will be best understood by reference to the following detailed description of a presently preferred embodiment of the invention, taken in conjunction with the drawing, in which:

FIG. 1, the sole FIGURE illustrates a vertical beam spectrophotometer which comprises a presently preferred embodiment of the invention.

DETAILED DESCRIPTION OF THE PRESENTLY PREFERRED EMBODIMENT

The detailed discussion which follows describes the invention in terms of a preferred vertical beam spectrophotometer which employs the broad aspects of the invention to specifically measure the light absorption of an enzyme immunoassay within a range of color densities up to approximately 2.2 optical density units. In addition, the preferred spectrophotometer is specifically adapted to measure assays which have a significant spectral component in the visible light range at about 460 nanometers, i.e., absorb a significant amount of 460 nanometer wavelength light and which have no or a negligible spectral component at 600 nanometers, i.e., absorb little or no 600 nanometer light. Specific examples of such assays include point-to-point assays such as AFP monoclonal and CEA monoclonal, cut-off assays such as HTLV III, auszyme, and corzyme, and similar rate assays. Each such assay is preferably labelled with an enzyme such as horse radish peroxidase and exposed to a chromophore such as OPD. Other enzymes such as alkaline phosphatase, beta-galatosidase, and urease are also suitable for use. It is understood, however, that the broad concept of the invention disclosed herein is not limited by the specific assays or wavelengths identified with respect to the preferred spectrophotometer but has broad applicability to any number of other assays which are now known or which may hereafter be developed, and to other wavelengths dependent upon the particular spectra of such assays.

With the foregoing in mind, FIG. 1 illustrates a vertical beam spectrophotometer 10 which comprises a presently preferred embodiment of the invention. The preferred spectrophotometer 10 comprises a light source 30, a selectable optical filter 40, an optical transmitting cable 55, one or more optical lenses 100, 105, and one or more corresponding optoelectronic detectors 120, 125.

Generally, the preferred spectrophotometer 10 measures an assay as follows: The light source 30 generates a beam of light which is filtered by the selectable optical filter 40 to remove all but a narrow band of wavelengths distributed about the center wavelength of the filter. The filtered light is conducted by the optical transmitting cable 55 and illuminates a portion of one or more solid phases such as beads 80, 85 in one or more corresponding reaction cuvettes 70, 75 each containing an assay to be measured. The term "solid phase" is used herein to refer to the bead 80, 85, i.e. the substrate or carrier, together with any layers adhered thereto. The beads 80, 85 diffuse the filtered light into the surrounding solutions 72, 77 and the lenses 100, 105 project the diffused light onto the optoelectronic detectors 120, 125. The optoelectronic detectors 120, 125 convert the projected light into electrical signals related to the optical development of the assays.

The light source 30 is preferably a white light generating display-type lamp such as the model number Q20MR16/FL (BAB) lamp manufactured by General Electric. The Q20MR16/FL BAB lamp is a 12-volt, 20 watt, tungsten-halogen lamp with an infrared dichroic reflector which reduces heat transmittance to the optical cable 55. The preferred lamp has a beam half angle of approximately 18 degrees and a center candlepower of approximately 460 lumens, which has been found suitable for measuring assays having color densities of up to approximately 2.2 optical density units. The spectrophotometer 10 may also be adapted to measure solutions with higher color densities by employing a light source with a higher output intensity, for example, increasing the sensitivity of the optoelectronic detector 120, 125 described below, or a combination of both. The preferred light source 30 is mounted in a housing 20 and is driven by a conventional 12-volt, constant current power supply 15.

The selectable optical filter 40 consists of a number of conventional interference filters 41–45. Each interference filter 41–45 has associated with it a front and a rear aperture each having a diameter of approximately 0.5 inches. A representative front aperture 41a and rear aperture 41b are identified in conjunction with interference filter 41. Preferably, two of the filters have center wavelengths of 460 and 600 nanometers respectively. The center wavelength values of the remaining filters are selected based upon the spectra of other particular assays that may be performed. The optical filter 40 is positioned between the light source 30 and the input 54 of the optical transmitting cable 55 such that whichever interference filter 41–45 is selected, its center will coincide with the optical center line 35 of the light beam.

A conventional stepper motor 50 is preferably used to position the selected interference filter 41–45 in the light beam. A conventional optical decoder/controller 52 is used to detect the precise position of the filter 40 and to control the stepper motor 50 to accomplish the precise positioning of the selected interference filter 41–45 in the beam. The structure and operation of the stepper motor 50 and optical decoder/controller 52 are matters within the knowledge of those skilled in the art. Accordingly, detailed descriptions thereof are not necessary for a complete understanding of the invention.

The optical transmitting cable 55 preferably has a main body 60 and five parallel branches, each directed to a cuvette containing an assay to be measured. Two representative branches, 61 and 65, and corresponding cuvettes 70 and 75 are illustrated in the FIGURE. The preferred optical cable 55 is comprised of 15,000–16,000 randomized glass fibers, has an acceptance angle of approximately 41 degrees, a numerical aperture of approximately 0.63–0.66, and a bandwidth of approximately 400 nanometers to 1400 nanometers. Each of the individual glass fibers preferably has a diameter of approximately 0.022 inches. The input 54 of the preferred optical cable 55 is approximately 0.29 inches in diameter and each of the outputs 62, 66 is approximately 0.125 inches in diameter. The light beams emerging from the outputs 62, 66 each have half angles of approximately 18 degrees. Preferably, the output intensity at any output varies no more than approximately ±5 percent from the output intensity at any other output. Thus, the measurement of a given assay will give essentially the sam result regardless of which output it is taken at. The ends of the fibers at the outputs 62, 66 are preferably parallel and are ground flat and polished to maximize the light transmitted to the cuvettes 70,75, as well as to reduce scattering and minimize noise. The length of the optical transmitting cable 55 is kept as short as possible to minimize light attenuation in the cable. A cable meeting the above requirements and therefore preferred for use is manufactured by Volpi Manufacturing, U.S.A. of Auburn, N.Y.

In order to maximize signal to noise ratio and the accuracy of the measurements, it is desirable to maximize the intensity of the light which the lenses 100 and 105 project onto the optoelectronic detectors 120, 125. Maximum light intensity is transmitted from the light source 30 to the cuvettes 70, 75 by positioning the input 54 of the optical cable 55 in close proximity to the selected interference filter 41–45 with its center coinciding with the optical center line 35 of the light beam and the plane of the input 54 being parallel to the plane of the selected interference filter 41–45. In addition, each of the outputs 62, 66 is positioned in close proximity to the bottom surface of the corresponding cuvette 70, 75 with its center coinciding with the optical center line 82, 84 of the corresponding lense 100, 105. The plane of each output 62, 66 is aligned perpendicularly to the corresponding optical center line 82, 84 of the corresponding lense 100, 105.

Specifically, it has been found that if the outputs 62, 66 of the optical transmitting cable 55 are positioned so that roughly the bottom one-third of each bead 80, 85 is illuminated, each bead will diffuse light having maximum intensity along the optical center line 82, 84. The beads 80, 85 also diffuse some light from their side surfaces but it has been found that the intensity of this light declines sharply in relation to the light diffused along the optical center line.

In illuminating the bottom surfaces of the cuvettes 70, 75, it is desirable to illuminate a relatively small section. This maximizes the light refracted into the beads 80, 85 and ensures that none of the light from the outputs 62, 66 passes directly into the solution 72, 77 or is refracted directly into the solution 72, 77 by the bottom surfaces of the cuvettes 70, 75. In the preferred embodiment, suitable illumination of the cuvettes 70, 75 and beads 80, 85 is obtained by positioning each output 62, 66 approximately 0.065 inches below the bottom surface of the corresponding cuvette 70, 75. Alternatively, the outputs 62, 66 could be positioned at a greater distance from the cuvettes 70, 75 and lenses used, for example, to reduce the area of illumination of the bottom surfaces of the cuvettes 70, 75 and beads 80, 85.

In the preferred embodiment, each of the cuvettes 70, 75 has the nominal dimensions illustrated in the FIGURE. Most importantly from the standpoint of illuminating the bottom third of the beads 80, 85 to provide maximum light intensity to the lenses 100, 105 and detectors 120, 125, the light-refracting bottom surfaces of the preferred cuvettes 70, 75 have a thickness of approximately 0.065 inches, an outer radius of approximately 0.212 inches, and an inner radius of approximately 0.157 inches. Each cuvette 70, 75 is positioned so that its center coincides with the optical center line of the corresponding lense 100, 105.

Each of the cuvettes 70, 75 may, of course, be a physically separate cuvette. However, the preferred spectrophotometer 10 embodying the invention is particularly suited for use in automated assay equipment. It is therefore contemplated that each of the outputs 62, 66 of the optical transmitting cable 55 would correspond to a reaction cuvette in one row of a conventional one-piece molded plastic reaction tray so that the spectrophotometer would measure a number of assay solutions simultaneously.

The preferred spectrophotometer 10 takes advantage of the light transmission and diffusion characteristics of conventional solid phase beads such as the ¼ and ⅜ inch spherical EIA beads manufactured by Abbott Laboratories. These beads are initially constructed of a substantially light-transmitting material such as polystyrene, for example. As part of the normal manufacturing process, the surfaces of the beads are finished to a randomly rough texture to facilitate chemical bonding thereto. This texture gives the beads a substantially translucent surface which provides substantial diffusion of light transmitted through the bead. Those skilled in the art will recognize that solid phases of different materials and shapes but with similar light transmission and diffusion characteristics are also suitable.

An optical lense and corresponding optoelectronic detector are positioned above each cuvette 70, 75. Representative lenses 100 and 105, and detectors 120 and 125, are illustrated. Each lense 100, 105 projects the light diffused by the corresponding bead 80, 85 onto the photosensitive surface of the corresponding detector 120, 125. Each detector 120, 125 generates an electrical signal, the magnitude of which is related to the intensity of the light projected on its surface.

In the preferred embodiment, each optical lense 100, 105 is an aspheric lense of crown glass having a 12 millimeter diameter and a focal point of 8.5 millimeters. Each lense is approximately 4 millimeters thick at its center point. Other lenses, such as holographic lenses, having the same optical properties as the lenses 100, 105 may also be used. Each lense 100, 105 is preferably positioned at a distance greater than its focal point from the corresponding detector 120, 125. Such positioning provides reduced sensitivity to variations in bead or cuvette position due to bubbles in the solution, misalignment of the reaction tray or other causes. It also tends to eliminate some effects caused by variations in the surfaces and coloration of the beads 80, 85.

Each optoelectronic detector 120, 125 is preferably a Hamamatsu S1336-8BQ silicon photocell or equivalent photocell. The Hamamatsu photocell is preferred for its relatively low cost, its linear current to light intensity response in the range of the wavelengths of interest, e.g. the center wavelengths of the filters 41–45, and its wide response range. However, the Hamamatsu photocell has been selected specifically for measuring assays having color densities ranging up to approximately 2.2 optical density units. A photocell or other optical-to-electrical converter having greater sensitivity may therefore be substituted if it is desired to measure assays with higher color densities.

In order to maximize the intensity of the light projected onto each detector 120, 125 in the preferred embodiment, lense 100, 105 and corresponding detector 120, 125 are mounted in a housing 90, 95 with the center of the detector 120, 125 coinciding with the optical center line 82, 84 of the corresponding lense 100, 105. Each housing 80, 85 has a lense aperture 92, 97 with a diameter of approximately 0.45 inches and a depth of approximately 0.20 inches, and a detector aperture with a diameter of approximately 0.25 inches and a depth of approximately 0.08 inches. The centers of both apertures are aligned with the optical center line of the corresponding lense 100, 105. Each lense 100, 105 is mounted with its center approximately 1.091 inches from the plane of the corresponding output 62, 64 of the optical cable 55. Each detector 120, 125 is mounted with its photosensitive surface perpendicular to the optical center line 82, 84 and approximately 1.157 inches from the center of the corresponding lense 100, 105. The internal diameter of each housing 90, 95 between the lense 100, 105 and the detector aperture 110, 115 is approximately the same as the diameter of the lense aperture 92, 97. The outputs of the detectors 120, 125 are connected to conventional processing circuitry (not shown), which does not form part of the present invention.

In operation, the light beam generated by the light source 30 passes through the selected interference filter 41–45 of the selectable filter 40. The light beam emerging from the selected interference filter 41–45 contains a narrow band of wavelengths distributed about the center wavelength of the filter within a range of approximately ten (10) nanometers above or below the center wavelength.

The filtered light enters the input 54 of the optical main transmitting cable 55 and is conducted down the main trunk 60 to each of the branches 61, 65. The filtered light emerges at the outputs 62, 66 and illuminates a small section of the bottom surfaces of the cuvettes 70, 75. The curved bottom surfaces of the cuvettes 70, 75 refract the filtered light to illuminate approximately the bottom one-third of the beads 80, 85. The beads 80, 85 diffuse the light into the surrounding solution 72, 77 with the maximum intensity of the light being diffused along the optical center lines 82, 84 of the lenses 100, 105.

The lenses 100, 105 project the light diffused by the beads 80, 85 onto the photosensitive surfaces of the optoelectronic detectors 120, 125. The optoelectronic detectors 120, 125 generate electrical signals that are related to the intensity of the light projected on their photosensitive surfaces and therefore to the light absorption of the assays. The electrical signals are processed in a known manner by conventional processing circuitry to determine the absorption value of the assay. The concentration of the antibody or antigen of interest in the original sample is calculated in a known manner from the absorption value.

As an example, assume that an enzyme immunoassay is prepared in each reaction cuvette 70, 75 of a conventional reaction tray using known solid phase, coated bead technology as described above. The outer layer of the bead is labelled with an enzyme such as horseradish peroxidase. A solution containing a chromophore such as OPD is added to each cuvette 70, 75 and the OPD reacts with the enzyme label and colors the solution blue. The concentration of the antigen or antibody of interest determines the color density of the solution, i.e., the degree of optical development of the solution.

The colored solution of the example has a peak absorbance value at 492 nanometers and a significant spectral component in the blue light range at 460 nanometers. The solution therefore will absorb light having a wavelength of 460 nanometers in relation to the optical density of the solution. It is preferable to measure the color density of the solution at 460 nanometers rather than at the peak absorbance value because the solution will absorb roughly half as much 460 nanometer light as it will 492 nanometer light of equal intensity. Accordingly, using 460 nanometer light to measure the assay allows the preferred spectrophotometer 10 to employ a lower intensity light source 30 and a less sensitive optoelectronic detector 120, 125 than would otherwise be required. The colored solution has either no or a negligible spectral component in the red light range at 600 nanometers and will therefore absorb little if any 600 nanometer light.

Preferably, before the OPD begins to react with the enzyme, the stepper motor 50 is operated to position the 460 nanometer interference filter into the light beam. The 460 nanometer light emerging from the filter is conducted by the optical cable 55, is diffused by the beads 80, 85 into the surrounding solution 72, 77 and is projected by the lenses 100, 105, onto the detectors 120, 125 which convert it into electrical signals having magnitude related to the absorption of the assay. An absorption measurement at 600 nanometers is taken in the same manner. In accordance with Beers Law, which is well known to those skilled in the art, the logarithm of the ratio of the 460 nanometer absorption value to the 600 nanometer absorption value is calculated. Since the 600 nanometer absorption value is approximately equal to one optical unit, the log of the ratio essentially gives a pre-optical development 460 nanometer absorption value for the assay.

After the assay has been incubated for a suitable time to allow it to optically develop, a second set of absorption measurements are made at 460 and 600 nanometers in the same manner as described above. On the second 460 nanometer measurement, the solution may absorb a greater percentage of the 460 nanometer light diffused by the beads 80, 85 depending on the concentration of the antibody or antigen of interest. The rest of the 460 nanometer light is projected by the lenses 100, 105, and is converted into electrical signals by the detectors 120, 125 as described. The log of the ratio of the 460 nanometer absorption value to the 600 nanometer absorption value is again calculated in accordance with Beer's Law to obtain a 460 nanometer post-development absorption value. The 460 nanometer pre-development absorption value is subtracted from the 460 nanometer post-development absorption value. The resulting 460 nanometer absorption value for the assay is independent of variations in various cuvette and bead parameters, which cancel out in the calculations. This absorption value is then used to determine the concentration of the antibody or antigen present in the assay in a known manner.

This exemplary procedure is preferably employed in measuring point-to-point assays such as those identified above. When measuring cut-off type assays, it is preferred to also take 460 and 600 nanometer measurements of a blank, calculate the log of the absorption ratio as described above and subtract this value from the 460 nanometer absorption value obtained according to the above-described procedure.

What have been described are certain aspects of a vertical beam spectrophotometer and method which constitute a presently preferred embodiment of the invention. It is understood that the foregoing description and accompanying illustration are merely exemplary and are in no way intended to limit the scope of the invention, which is defined solely by the appended claims. Various changes and modifications to the preferred embodiment will be apparent to those skilled in the art. For example, it is understood that the invention has broad application to many assays and is not limited to the specific exemplary assays identified herein, to the specific wavelengths corresponding thereto, or to the specific exemplary optical density range identified. Various component substitutions may also be made including, for example, replacing the detector 120, 125 with a different or more sensitive optical to electrical converter, replacing the optical cable 55 with light guides or the like, employing a higher intensity light source, or replacing the lense 100, 105 with other light projecting components. Various dimensions may also be varied to optimize performance of the preferred spectrophotometer for different assays and different optical density ranges. All such variations, modifications, and substitutions can be made without departing from the spirit and scope of the invention. Accordingly, it is intended that all such variations, modifications, and substitutions, and all other equivalents be covered by the appended claims.

We claim:

1. A spectrophotometer for measuring an assay having a solid phase in solution, comprising:
   means for illuminating at least a portion of said solid phase to cause said solid phase to diffuse light into said solution;
   optical means for projecting at least a portion of the light diffused by said solid phase; and
   optoelectronic means for converting said projected light into an electrical signal having a parameter related to the light absorption of said assay.

2. The spectrophotometer defined in claim 1 wherein said means for illuminating comprises:
   means for generating a beam of light having a selected band of wavelengths; and
   means for conducting said light beam to illuminate at least a portion of said solid phase.

3. The spectrophotometer defined in claim 1 wherein said solid phase is comprised of a substantially light-transmitting material having a surface that substantially diffuses light.

4. The spectrophotometer defined in claim 1 wherein said optical means comprises lense means.

5. A spectrophotometer for measuring an assay having a solid phase in solution, comprising:
   means for illuminating at least a portion of said solid phase along a selected optical line to cause said solid phase to diffuse light into said solution substantially along said optical line;
   optical means positioned along said optical line for projecting at least a portion of the light diffused by said solid phase along said optical line; and
   optoelectronic means positioned along said optical line for converting said projected light into an electrical signal having a parameter related to the light absorption of said assay.

6. The spectrophotometer defined in claim 5 wherein said means for illuminating comprises:
   means for generating a beam of light having a selected band of wavelengths; and
   means for conducting said light beam to illuminate said portion of said solid phase substantially along said selected optical line.

7. The spectrophotometer defined in claim 5 wherein said solid phase comprises a substantially light-transmitting material having a surface that substantially diffuses light.

8. The spectrophotometer defined in claim 5 wherein said optical means comprises lense means.

9. A spectrophotometer for simultaneously measuring a plurality of assays having a corresponding plurality of solid phases in solution, comprising:
   means for simultaneously illuminating at least a portion of each of said plurality of solid phases to cause each of said solid phases to diffuse light into said solution;
   a plurality of optical means each corresponding to one of said plurality of solid phases for projecting at least a portion of the light diffused by each of said solid phases; and
   a plurality of optoelectronic means each corresponding to one of said plurality of optical means for converting the light projected by said corresponding optical means into a corresponding plurality of electrical signals each having a parameter related to the light absorption of the corresponding assay.

10. The spectrophotometer defined in claim 9 wherein said means for illuminating comprises:
    means for generating a beam of light having a selected band of wavelengths; and
    means for conducting said light beam to simultaneously illuminate at least a portion of each of said plurality of solid phases.

11. The spectrophotometer defined in claim 9 wherein each said solid phase is comprised of a substantially light-transmitting material having a surface that substantially diffuses light.

12. The spectrophotometer defined in claim 9 wherein each said optical means comprises a lense means.

13. A spectrophotometer for simultaneously measuring a plurality of assays having a corresponding plurality of solid phases in solution, comprising:
    means for simultaneously illuminating at least a portion of each of said plurality of solid phases along a selected optical line to cause each of said solid phases to diffuse light into said solution substantially along said optical line;
    a plurality of optical means corresponding to said plurality of solid phases positioned along said optical line for projecting at least a portion of the light diffused by said corresponding solid phase along said optical line; and
    a plurality of optoelectronic means positioned along said optical line each corresponding to one of said plurality of optical means for converting the light projected by each said corresponding optical means into a corresponding plurality of electrical signals each having a parameter related to the light absorption of the corresponding assay.

14. The spectrophotometer defined in claim 13 wherein said means for illuminating comprises:
    means for generating a beam of light having a selected band of wavelengths; and
    means for conducting said light beam to illuminate said portion of each of said plurality of solid phases substantially along said optical line.

15. The spectrophotometer defined in claim 13 wherein each said solid phase is comprised of a substantially light transmitting material having a surface that substantially diffuses light.

16. The vertical beam spectrophotometer defined in claim 13 wherein each said optical means comprises lense means.

17. A spectrophotometer for measuring an assay including a solid phase and a surrounding solution in a cuvette means comprising:
    means for generating a light beam having a selected band of wavelengths;
    means for directing said light beam onto a portion of a surface of said cuvette means along a selected optical line, said surface of said cuvette means being adapted to direct light onto a portion of said solid phase to cause said solid phase to diffuse light into said surrounding solution substantially along side optical line;
    lense means positioned along said optical line for projecting at least a portion of the diffused light; and
    optoelectronic means positioned along said optical line for converting said projected light into an electrical signal having a parameter related to the light absorption of said assay.

18. A method for measuring an assay having a solid phase in solution, comprising the steps of:
    (a) generating a light beam;

(b) illuminating at least a portion of said solid phase with said light beam to cause said solid phase to diffuse light into said solution;
(c) projecting at least a portion of the light diffused by said solid phase; and
(d) converting the projected light into an electrical signal having a parameter related to the light absorption of said assay.

19. The method defined in claim 18 wherein the step of generating a light beam comprises generating a light beam having a selected band of wavelengths.

* * * * *